United States Patent
Brannon

(10) Patent No.: US 9,649,124 B2
(45) Date of Patent: May 16, 2017

(54) CURVED BLADE TISSUE SHAVER

(71) Applicant: James K Brannon, Leawood, KS (US)

(72) Inventor: James K Brannon, Leawood, KS (US)

(*) Notice: Subject to any disclaimer, the term of this patent is extended or adjusted under 35 U.S.C. 154(b) by 75 days.

(21) Appl. No.: 14/157,357

(22) Filed: Jan. 16, 2014

(65) Prior Publication Data

US 2015/0196314 A1    Jul. 16, 2015

(51) Int. Cl.
*A61B 17/32*    (2006.01)

(52) U.S. Cl.
CPC ........... *A61B 17/32002* (2013.01); *A61B 2017/320028* (2013.01); *A61B 2017/320032* (2013.01)

(58) Field of Classification Search
CPC ........................................ A61B 17/32; A61B 2017/320004–2017/320012; A61B 17/320016; A61B 17/32002; A61B 2017/320024; A61B 2017/320028; A61B 2017/320032; A61B 17/320068; A61B 17/320783; A61B 2017/320064; A61B 2017/320072; A61B 2017/320076; A61B 2017/32008; A61B 2017/320084; A61B 2017/22038; A61B 2017/22039; A61B 2017/22041; A61B 2017/22042; A61B 2017/22045; A61B 2017/22047

See application file for complete search history.

(56) References Cited

U.S. PATENT DOCUMENTS

| | | | | |
|---|---|---|---|---|
| 4,646,738 | A | * | 3/1987 | Trott ................ A61B 17/32002 600/565 |
| 4,986,807 | A | * | 1/1991 | Farr ............... A61B 17/320783 604/22 |
| 2007/0276419 | A1 | * | 11/2007 | Rosenthal ................ 606/159 |
| 2013/0110145 | A1 | * | 5/2013 | Weitzman .......... A61B 17/3205 606/170 |
| 2013/0274751 | A1 | * | 10/2013 | Steinwachs ............ A61B 17/16 606/84 |

OTHER PUBLICATIONS

U.S. Appl. No. 10/928,553, Aug. 26, 2004, James Kevin Brannon.
U.S. Appl. No. 11/970,246, Jan. 7, 2008, James K. Brannon.
U.S. Appl. No. 12/369,388, Feb. 11, 2009, James K. Brannon.
U.S. Appl. No. 12/181,205, Jul. 28, 2008, James K. Brannon.
U.S. Appl. No. 12/369,575, Feb. 11, 2009, James K. Brannon.
U.S. Appl. No. 12/706,706, Feb. 6, 2010, James K. Brannon.
U.S. Appl. No. 13/361,823, Jan. 30, 2012, James K. Brannon.
U.S. Appl. No. 61/170,508, Apr. 17, 2009, James K. Brannon.
U.S. Appl. No. 61/253,068, Oct. 20, 2009, James K. Brannon.
U.S. Appl. No. 61/218,757, Jun. 19, 2009, James K. Brannon.

(Continued)

*Primary Examiner* — Jonathan Miles
*Assistant Examiner* — Kankindi Rwego
(74) *Attorney, Agent, or Firm* — Intellectual Property Center, LLC; Arthur K. Shaffer

(57) ABSTRACT

The present invention provides an improved curved blade shaver for abriding tissue associated with a surgical site, the curved blade assembly including a curved outer shaft in receipt of an substantially linear inner instrument having a flexible region adapted for rotation and reciprocal receipt within the curved outer shaft and presenting a shaving means for debriding the tissue. The curved outer shaft also includes a portal for reciprocal receipt of a substantially rigid instrument when desired.

8 Claims, 3 Drawing Sheets

(56) References Cited

OTHER PUBLICATIONS

U.S. Appl. No. 61/266,908, Dec. 4, 2009, James K. Brannon.
U.S. Appl. No. 61/266,900, Dec. 4, 2009, James K. Brannon.
U.S. Appl. No. 61/303,496, Feb. 11, 2010, James K. Brannon.
U.S. Appl. No. 61/303,508, Feb. 11, 2010, James K. Brannon.
U.S. Appl. No. 61/309,732, Mar. 2, 2010, James K. Brannon.
U.S. Appl. No. 61/319,166, Mar. 30, 2010, James K. Brannon.
U.S. Appl. No. 61/325,084, Apr. 16, 2010, James K. Brannon.
U.S. Appl. No. 61/325,102, Apr. 16, 2010, James K. Brannon.
U.S. Appl. No. 12/763,213, Apr. 20, 2010, James K. Brannon.
U.S. Appl. No. 12/820,133, Jun. 21, 2010, James K. Brannon.
U.S. Appl. No. 12/908,879, Oct. 21, 2010, James K. Brannon.
U.S. Appl. No. 12/961,487, Dec. 6, 2010, James K. Brannon.
U.S. Appl. No. 12/961,491, Dec. 6, 2010, James K. Brannon.
U.S. Appl. No. 12/986,064, Jan. 6, 2011, James K. Brannon.
U.S. Appl. No. 61/443,655, Feb. 16, 2011, James K. Brannon.
U.S. Appl. No. 61/444,025, Feb. 17, 2011, James K. Brannon.
U.S. Appl. No. 61/444,315, Feb. 18, 2011, James K. Brannon.
U.S. Appl. No. 61/645,327, May 23, 2013, James K. Brannon.
U.S. Appl. No. 13/444,559, Apr. 11, 2012, James K. Brannon.
U.S. Appl. No. 13/039,191, Mar. 2, 2011, James K. Brannon.
U.S. Appl. No. 13/076,408, Mar. 30, 2011, James K. Brannon.
U.S. Appl. No. 13/089,306, Apr. 18, 2011, James K. Brannon.
U.S. Appl. No. 13/197,476, Aug. 3, 2011, James K. Brannon.
U.S. Appl. No. 13/838,330, Mar. 15, 2013, James K. Brannon.
U.S. Appl. No. 13/844,652, Mar. 15, 2013, James K. Brannon.
U.S. Appl. No. 61/839,152, Jun. 25, 2013, James K. Brannon.
U.S. Appl. No. 13/944,696, Jul. 17, 2013, James K. Brannon.
U.S. Appl. No. 61/891,836, Oct. 16, 2013, James K. Brannon.

* cited by examiner

CURVED BLADE TISSUE SHAVER

FIELD OF THE INVENTION

The present invention is broadly directed to improvements in instruments for arthroscopic surgery and, more particularly, to a rotating shaver blades for use in various endoscopic surgical procedures.

BACKGROUND OF THE INVENTION

Modern surgery tends toward minimally invasive techniques whenever possible because they reduce pain and accelerate healing. Although often more complicated in some ways for the surgeon, minimally invasive techniques result in less trauma to the patient and less scarring because of much smaller incisions thereby promoting faster healing and reducing possibilities for infections. In general, minimally invasive surgeries involve making one or more small incisions at appropriate locations and inserting tubular devices through the incisions to the surgical site.

The repair, as well as the replacement, of diseased and damaged tissue at a surgical site on or within a patients body is currently preformed using mechanical surgical instruments including simple scalpels which are used for cutting soft tissue, rotable shavers which are also used for removing soft tissue and rotatable burrs which are used for cutting harder tissue such as bone. Elongated surgical cutting instruments are generally known.

In closed surgery such as arthroscopic or more generally, endoscopic surgery, access to the surgical site is gained using one or more portals, and instruments and scopes which are inserted through the incision to the surgical site. Some of these instruments include elongated rotary shavers which have a straight, elongated outer surface and an elongated inner cylincrical member which is concentrically disposed within the outer tubular member. The inner and outer members are sometimes separately and jointly referred to as "blades" or "shavers" and are usually disposable.

In some rotary shavers, each of the shaving members has a proximal and distal end with the proximal end being adapted for rotation by a rotary drive means with a reusable handpiece. The distal end of the inner tubular member may have a cutting means or cutting edge for removal of tissue. In some cases, the distal cutting means cooperates with the opening in the outer member to remove tissue. In some cases rotary burrs are used to selectively affect the tissue. When these elongated instruments are used, they may become clogged with the affected tissue thereby limiting the effectiveness of these instruments during the surgical procedure.

In addition, some of these elongated surgical cutting instruments may utilize a straight or angled shaft. The shaft having the straight configuration may allow for ready removal of the inner cutting instrument from the outer shaft. Allowing for removal of clogged debris or replacement of the inner cutting instrument. However some angled instruments have limitations which prevent removal of the inner cutting instrument form the outer shaft. Utilizing an angled configuration may prevent ready removal and replacement of the inner instrument. It would be desireable to provide a readily removable and replaceable inner instrument during a surgical procedure where the outer member may be cleared of clogging debris or the inner instrument could be replaced with an additional instrument or for use with a nitinol guide wire to maintain the incision during exchange of the inner instrument and outer shaft as desired. In this way, the present invention may help limit the damage caused to the surrounding tissue by unnecessary incisions by requiring new passageways to the surgical site every time the instrument is removed or cleared.

In traditional rotary shaver operation, the inner member rotates in relation to the outer member for cutting the tissue and aspirating it via a vacuum source connected to the proximal end. However, during operation the shaver may become clogged with debrided tissue thereby frustrating the aspirating operation. In a straight shaver instrument often the inner instrument can be removed or a rigid instrument inserted therein for removal of the lodged debris. With a shaving having an angled configuration, running a rigid instrument therethrough is unlikely. Additionally, removal of the inner instrument to remove the lodged debris is also unlikely. Once clogged the shaver apparatus is effectively unusable and a replacement assembly may be required. Because removal of the inner instrument is unlikely, the most common way to dislodge the debris would be to remove the entire shaver apparatus during the procedure, thereby losing the incision and the surgical site becoming inaccessible. Once a new shaver assembly is obtained, then returning to the surgical site may require additional incisions leading to unnecessary and redundant tissue trauma. It therefore would be desirable to have a fixed angle shaver having the ability to remove the inner instrument without loss of the surgical passage. Additionally, it would be beneficial to have a angled shaver adapted for receipt of a rigid instrument within the outer shaft of the shaver member.

During operation of the conventional rotary shaver, the inner blade has a cutting surface which is rotated. Some inner blades are hollow and allow for aspiration, however, the aspiration typically only works when the cutting surface is positioned facing the surgical site. When the cutting surface is rotated within the outer shaft aspiration may not occur or if it occurs, only occurs periodically and not continuously during use. The fluid may surge through the shaver and when the procedure is complete, tissue or other debris may be inadvertently left in the shaver depending on the rotation cycle of the inner blade. It therefore would be beneficial to allow for continuous aspiration of the surgical site through the shaver.

SUMMARY OF THE INVENTION

The invention is defined by the appended claims with a specific embodiment shown in the attached drawing. For the purpose of summarizing the invention, the invention is incorporated into a curved shaver assembly and includes a curved outer shaft in receipt of an substantially linear inner instrument having an inner proximal and distal ends separated by a flexible region adapted for rotation and reciprocal receipt within the curved outer shaft, the inner distal end in collaboration with the outer distal end presenting a shaving means for debriding tissue at the surgical site. The inner proximal end is connectably secured to a conventional handpiece in receipt of a conventional rotatable hub which is adapted for operation by a rotational drive (not shown) enabling a shaving means to cut tissue (not shown) of a patient (not shown) upon rotation of the inner instrument relative to the outer shaft. The curved outer shaft presents an inwardly and outwardly facing surfaces, the outwardly facing surface presenting a portal for reciprocal receipt of a substantially rigid instrument (not shown) therethrough. A central lumen extending along the received inner instrument provides for fluidic communication between the surgical site and the proximal ends for removing tissue debrided by the shaving means thereat.

Ther outer shaft includes a portal for reciprocal receipt of a substantially rigid instrument (not shown). The inner instrument includes a flexible region which is spaced between the inner distal end and inner proximal end and is adapted for rotation and reciprocal removal from the outer shaft.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
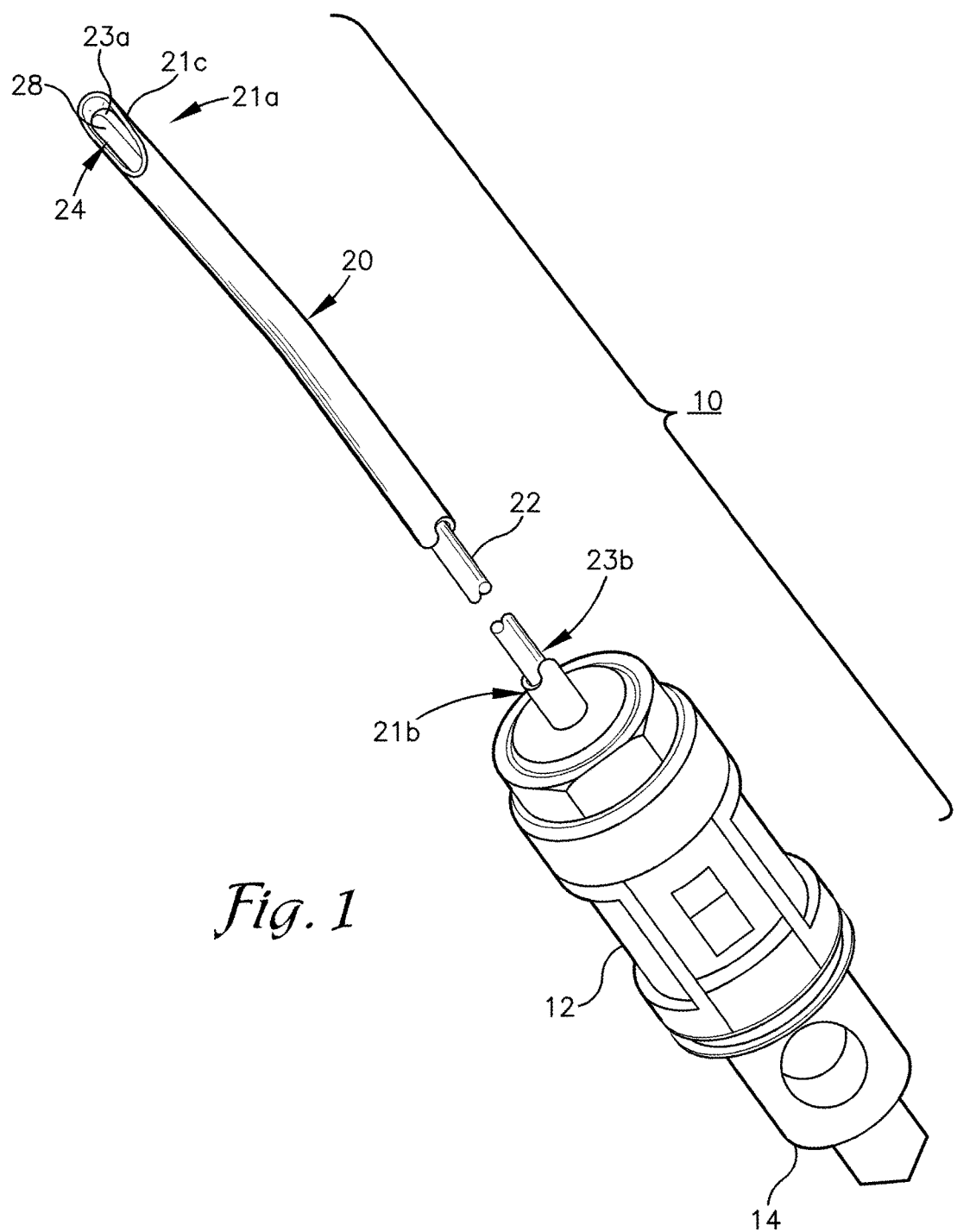
FIG. 1 is a partial side perspective of an embodiment of the present invention.

Referring to the drawings in more detail, FIG. 1 generally designates an embodiment of the curved shaver assembly generally referred to herein by reference numeral 10 formed in accordance with a first embodiment of the invention. The illustrated curved shaver assembly 10 includes an outer shaft 20 having an outer proximal end 21b and an outer distal end 21a and an inner instrument 22 having an inner proximal end 23b and an inner distal end 23a, the inner instrument 22 being received by the outer shaft 20. The inner distal end 23a has shaving means 24 for abriding tissue (not shown). The inner proximal end 23b is connectably secured to a conventional handpiece 12 in receipt of a conventional rotatable hub 14 which is adapted for operation by a rotational drive (not shown) enabling the shaving means 24 to cut tissue (not shown) of a patient (not shown) upon rotation of the inner instrument 22 relative to the outer shaft 20. The inner instrument 22 includes a flexible region 26 to be described in more detail hereinafter which may extend substantially the length of the outer shaft 20 or be spaced between the inner distal end 23a and inner proximal end 23b and is adapted for removal from the outer shaft 20.

Figure 2:
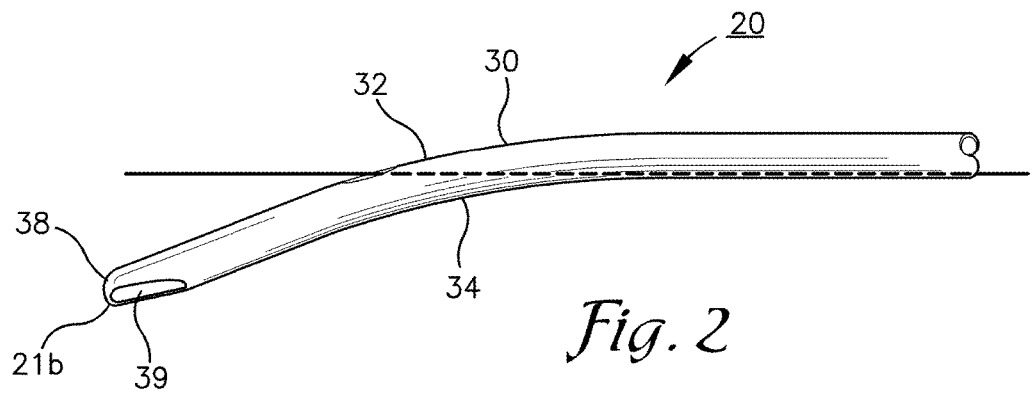
FIG. 2 is fragmented side elevation of the outer sheath depicted in the embodiment of FIG. 1.
Figure 4:
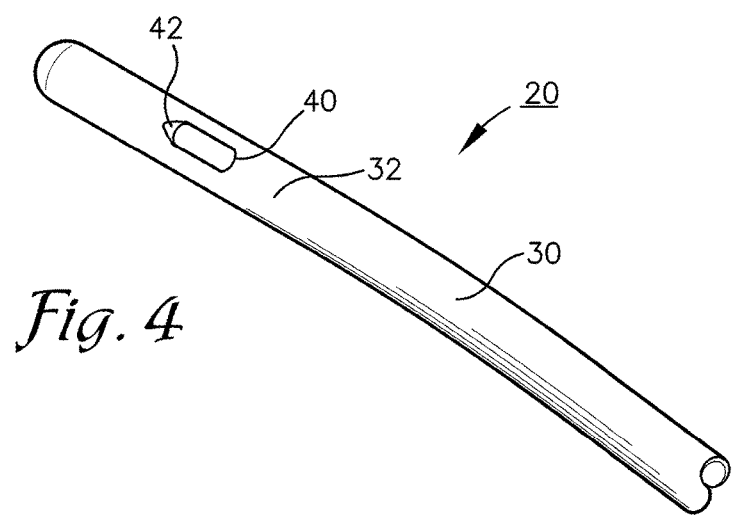
FIG. 4 is a fragmented bottom plan view of an outwardly facing surface consistent with the embodiment of the outer sheath of FIG. 2.

The outer shaft 20 includes an angled region 30 to facilitate placement of the surgical instrument at a surgical site (not shown). In one embodiment the depicted angled region 30 will have an angular spacing between 5 deg. and 85 deg with the angled region 30 illustrated in FIG. 2 being closer to 25 deg. although angled surgical instruments are generally known and the invention is therefore not limited to such an angular orientation. The outer shaft 20 is generally fabricated from a rigid material to maintain its shape during use and depending on the characteristics of the procedure being performed may be more or less severe. As depicted in FIG. 2, the outer shaft 20 has an inner facing surface 34 with an acute angle and an outer facing surface 32 with a reflex angle. The outer facing surface 32 is further depicted in FIG. 4 with a port 40. The port 40 is positioned to allow for receipt of a non-flexible instrument (not shown) such as but not limited to a guide wire or other rigid instrument which may be used to remove any lodged debris or to maintain the surgical passageway during removal of the assembly 10 from the surgical site and facilitate relocation of the assembly to the surgical site as desired. The port 40 further includes a guide to facilitate alignment of the guide wire through the portal towards the surgical site.

The shaving means generally designated 24 includes an inner cutting surface 23c associated with an inner channel 28 located at the inner distal end 23a and an outer cylindrical sidewall 21c associated with the outer distal end 21a such that rotation of the shaving means within the outer distal end 21a of the outer shaft 20 enables tissue disposed in the vicinity of the outer shaft sidewall 21c to be sheared by the interaction of the inner cutting surface 23c and the outer shaft sidewall 21c.

The flexible region 26 associated with the inner instrument 22 is adapted for facilitating removable receipt of the inner instrument 22 from the angled outer shaft 20. The inner instrument 22 may be fabricated from a variety of materials, including but not limited to use of stainless steel materials with the inner proximal and distal ends 23b, 23a utilizing a cylindrical configuration separated by the flexible region 26. The flexible region 26 in the depicted embodiment of FIG. 3 may include a single stainless steel cable or an interlaced structure with a plurality of stainless steel cables extending between and joining the inner proximal and distal ends 23b, 23a while allowing for angular displacement of the inner channel 28 within the outer shaft 20 and rotation therein. More specifically, the plurality of steel cables may be wound, interaced or extended as desired to provide the necessary elasticity for reciprocal and rotational movement within the outer shaft 20 depending on the characteristics of the flexible region 26. The steel cables may be secured to the inner proximal and distal ends 23b, 23a using traditional securing methods, including mechanical, thermal and chemical means which permit rotational and reciprocal movement of the inner instrument 22 within the outer shaft 20. The inner instrument 22 includes a central lumen 36 extending therethrough from the conventional handpiece, through the flexible region to the inner channel for aspiration or irrigation of the debrided tissue therethrough during operation of the shaving means 24 as desired at the surgical site.

The curved shaver assembly 10 of the present invention generally includes a curved outer shaft 20 in inner receipt of an substantially linear inner instrument 22 having an inner proximal and distal ends 23b, 23a separated by a flexible region 26 adapted for rotation and reciprocal receipt within the curved outer shaft 20, the inner distal end 23a in collaboration with the outer distal end 21b presenting a shaving means for debriding tissue at the surgical site. The curved outer shaft 20 presents an inwardly and outwardly facing surfaces 34, 32, the outwardly facing surface 32 presenting a portal 40 for reciprocal receipt of a substantially rigid instrument (not shown) therethrough. A central lumen 36 extending along the received inner instrument 22 provides for fluidic communication between the surgical site and the proximal ends 21b, 23b for removing tissue debrided by the shaving means 24 thereat.

The outer distal end 21a is depicted in FIG. 1 presents a carrier 38 with a window 39 thereat. The carrier 38 overlies the tip of the inner distal end 23a during movement of the assembly 10 to prevent unnecessary damage during operation. The window 39 is designed for engagement of surrounding tissue during tissue debridement while the carrier 38 provides the necessary sidewall structure for tissue debridement while housing the inner distal tip 23a. The inner distal end 23a may also include channel 28 as depicted in FIG. 3 which extends outwardly from the inner instrument 22 to promote fluidic communication at the surgical site (not shown).

Figure 5:
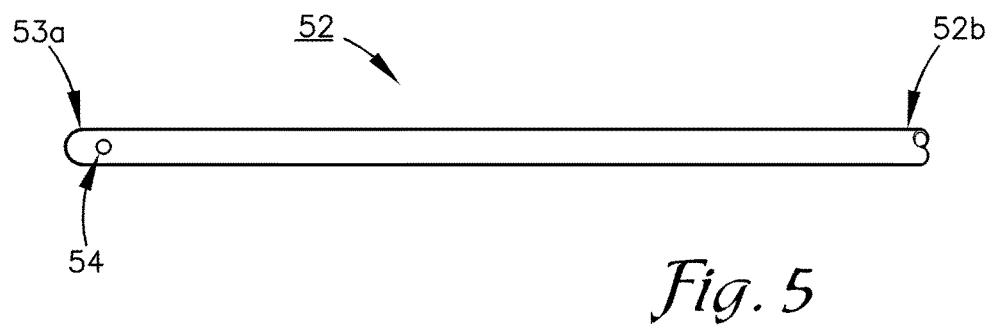
FIG. 5 is a fragmented bottom plan view of an alternative inner instrument.

An alternative embodiment of the inner instrument 52 is depicted in FIG. 5 in which the inner instrument 52 includes an aperture 54 being spaced from the inner channel 28. The aperture 54 may be used to provide more regular fluid flow during rotation of the inner instrument 52 such as, but not limited to, the aspiration procedure. The aperture 54 is depicted as being circular and located on a dorsal side of the inner instrument 52. However, the aperture 54 may alternatively be positioned or shaped as desired including elongated, irregular or having a plurality. In operation, as a inner proximal end 52b of the inner instrument 52 is rotated the distal end 53a rotates within the outer shaft 20. During aspiration, the rotary drive (not shown) engages the rotatable hub 14 causing the inner instrument 52 to rotate allowing the inner distal end 53a to alternately present the inner channel 28 and the aperture 54 at the window 39 during rotation. In this manner, during aspiration the tissue will be debrided from the surgical site and transported along the lumen out the back of the handpiece 12. Alternative placement of the aperture 54 may be utilized to preferentially affect the fluid flow while transporting the debrided tissue along the lumen 36 during the aspiration procedure.

Figure 3:
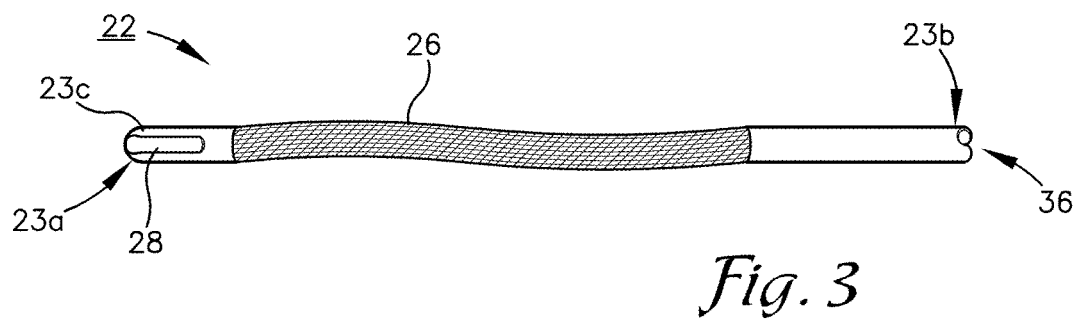
FIG. 3 is a fragmented side elevation of an inner instrument consistent with the depiction in the embodiment of FIG. 1.
Figure 6:
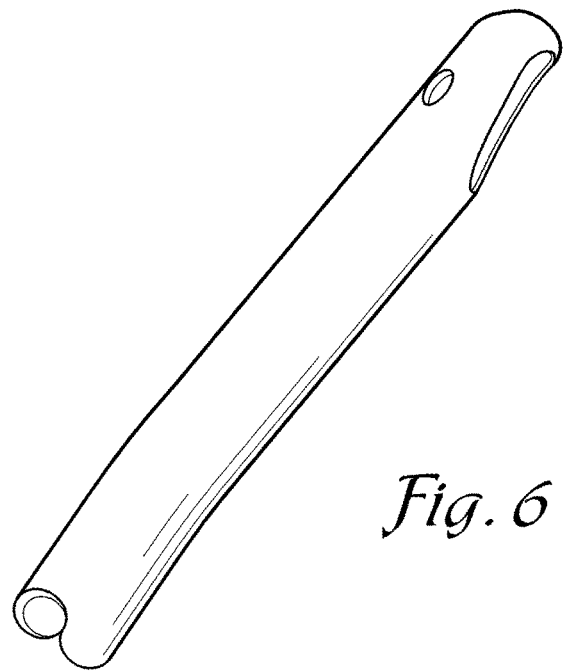
FIG. 6 is a fragmented perspective view of an alternative linear outer shaft.

Another alternative embodiment may include a substantially linear outer shaft as depicted in FIG. 6, having a proximal and distal end, the proximal end being positioned near the inner proximal end and the distal end having a carrier 38 for debridement of tissue while housing the alternative inner instrument 52 of FIG. 5 having the aperture spaced opposite the channel 28—illustrated in FIG. 3—which while the inner instrument is rotated provides for regular fluid flow along the lumen during rotation of the alternative inner instrument 52 while the surgical site is aspirated.

In operation and use of the curved shaver assembly 10 as described hereinbefore, the present invention provides a significant improvement over the prior art devices particularly when debriding tissue in areas that are difficult to access and commonly clog typical shavers and for procedures which require multiple instruments so that the instruments may be utilized in the same incision during the surgical procedure without requiring multiple incisions to utilize a plurality of surgical instruments.

It is to be understood that while certain forms of the present invention have been illustrated and described herein, it is not to be limited to the specific forms or arrangement of parts described and shown and that numerous changes in the details of construction and the combination and arrangement of parts may be resorted to without departing from the spirit and scope of the invention. The present disclosure includes that contained in the appended claims as well as that of the forgoing description and drawings.

What is claimed and desired to be secured by Letters Patent is:

1. An improved curved blade shaver assembly comprising:
   a hollow outer shaft having a substantially straight distal end separated from a substantially straight proximal end by an angled region;
   a rotatable inner instrument received by said hollow outer shaft and having an inner distal end separated from an inner proximal end by a flexible region adapted for reciprocal movement along said angled region;
   said distal end presenting a carrier and a window, said carrier housing said inner distal end during placement at a surgical site said window presenting a shaving means for debriding tissue at the surgical site whereby said debrided tissue travels along a central lumen extending along said inner instrument between a handpiece and said inner distal end;
   a portal on the angled region of the hollow outer shaft, spaced from said carrier and opposite said window; and
   a rigid instrument extending along said outer shaft and through said portal.

2. The curved blade shaver assembly of claim 1 wherein said portal farther comprises a guide.

3. The curved blade shaver assembly of claim 1 wherein said inner distal end presents an inner channel.

4. The curved blade shaver assembly of claim 1 wherein said angled region is angled from between 5 deg and 85 deg from a central axis extending through said proximal end.

5. The curved blade shaver assembly of claim 1 wherein said flexible region is further comprised. of a plurality of steel cables.

6. The curved blade assembly of claim 5 wherein said steel cables circumvent said lumen.

7. The curved blade shaver assembly of claim 1 wherein said inner instrument further comprises an aperture spaced opposite a channel at said inner distal end wherein said aperture and channel are alternately presented at said window during rotation of said inner instrument.

8. An improved curved blade shaver assembly comprising:
   a hollow outer shaft having a substantially straight distal end separated from a substantially straight proximal end by an angled region;
   said hollow shaft adapted for receipt of a first and second instrument,
   said second instrument comprising a flexible rotatable inner instrument having an inner distal end separated from an inner proximal end by a flexible region adapted for reciprocal movement along said angled region;
   said distal end presenting a carrier and a window, said carrier housing said inner distal end during placement at a surgical site said window presenting a shaving means for debriding tissue at the surgical site;
   a portal on the angled region of the hollow outer shaft, spaced from said carrier and opposite said window;
   a rigid instrument extending along said outer shaft and through said portal; and
   said first instrument comprising a rigid elongated guide adapted for reciprocal movement through said portal.

* * * * *